US011000248B2

(12) United States Patent
Gadenne et al.

(10) Patent No.: US 11,000,248 B2
(45) Date of Patent: May 11, 2021

(54) SYSTEMS AND METHODS FOR ACCELERATING TRANSITIONS FOR DUAL ENERGY COMPUTED TOMOGRAPHY IMAGING (71) Applicant: GE Precision Healthcare LLC, Milwaukee, WI (US)

(72) Inventors: Aurelien Gadenne, Le Bouscat (FR); Benoit Grigis, Versailles (FR); Jean-François Larroux, Chaville (FR); Elie Herve, Villiers le Bacle (FR)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 50 days.

(21) Appl. No.: 16/592,619

(22) Filed: Oct. 3, 2019

(65) Prior Publication Data

US 2021/0100517 A1    Apr. 8, 2021

(51) Int. Cl.
*A61B 6/00* (2006.01)
(52) U.S. Cl.
CPC .............. *A61B 6/482* (2013.01); *A61B 6/405* (2013.01); *A61B 6/42* (2013.01); *A61B 6/5211* (2013.01); *A61B 6/54* (2013.01)
(58) Field of Classification Search
CPC ........... A61B 6/482; A61B 6/42; A61B 6/405; A61B 6/54; A61B 6/5211
See application file for complete search history.

(56) References Cited

U.S. PATENT DOCUMENTS

| 8,340,250 | B2 | 12/2012 | Lemaitre et al. | |
|---|---|---|---|---|
| 9,253,864 | B2 | 2/2016 | Caiafa et al. | |
| 2010/0183117 | A1* | 7/2010 | Tsumuraya | H05G 1/58 378/9 |
| 2010/0303196 | A1* | 12/2010 | Zou | A61B 6/542 378/5 |
| 2016/0192465 | A1* | 6/2016 | Larroux | G01N 23/046 378/4 |
| 2020/0359987 | A1* | 11/2020 | Fan | A61B 6/544 |

* cited by examiner

*Primary Examiner* — Marcus H Taningco
(74) *Attorney, Agent, or Firm* — McCoy Russell LLP (57) ABSTRACT

Methods and systems are provided for dual energy imaging. In one embodiment, a method comprises controlling an x-ray source with a first voltage to generate x-rays at a first energy, controlling the x-ray source with a second voltage to generate x-rays at a second energy lower than the first energy, and controlling a current of the x-ray source to peak above a target current when a voltage of the x-ray source is transitioning from the first voltage to the second voltage. In this way, the duration for transitioning from the first voltage to the second voltage is reduced, thereby enabling faster voltage switching of the x-ray source, improved energy separation in acquired projection data, and improved image quality.

20 Claims, 7 Drawing Sheets

SYSTEMS AND METHODS FOR ACCELERATING TRANSITIONS FOR DUAL ENERGY COMPUTED TOMOGRAPHY IMAGING

FIELD

Embodiments of the subject matter disclosed herein relate to medical imaging systems, and more particularly, to dual energy techniques for computed tomography (CT) imaging systems.

BACKGROUND

Dual or multi-energy spectral computed tomography (CT) systems can reveal the densities of different materials in an object and generate images acquired at multiple monochromatic x-ray energy levels. In the absence of object scatter, a system derives the behavior at a different energy based on a signal from two regions of photon energy in the spectrum: the low-energy and the high-energy portions of the incident x-ray spectrum. In a given energy region of CT, two physical processes dominate the x-ray attenuation: Compton scattering and the photoelectric effect. The detected signals from two energy regions provide sufficient information to resolve the energy dependence of the material being imaged. Detected signals from the two energy regions provide sufficient information to determine the relative composition of an object composed of two hypothetical materials.

BRIEF DESCRIPTION

In one embodiment, a method comprises controlling an x-ray source with a first voltage to generate x-rays at a first energy, controlling the x-ray source with a second voltage to generate x-rays at a second energy lower than the first energy, and controlling a current of the x-ray source to peak above a target current when a voltage of the x-ray source is transitioning from the first voltage to the second voltage. In this way, the duration for transitioning from the first voltage to the second voltage is reduced, thereby enabling faster voltage switching of the x-ray source, improved energy separation in acquired projection data, and improved image quality.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 4:
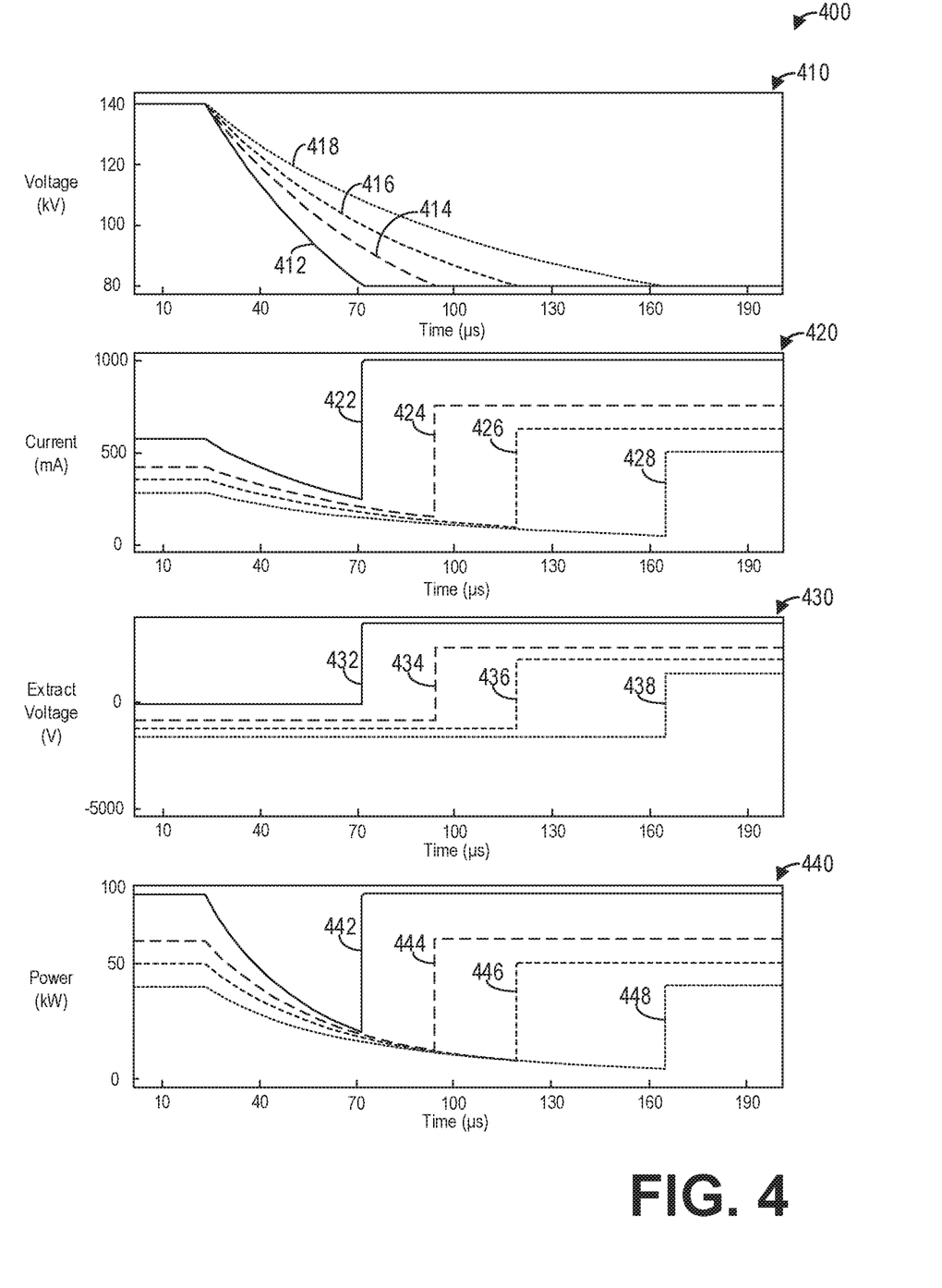
FIG. 4 shows a set of graphs illustrating x-ray generation parameters for dual energy imaging according to an embodiment.
Figure 5:
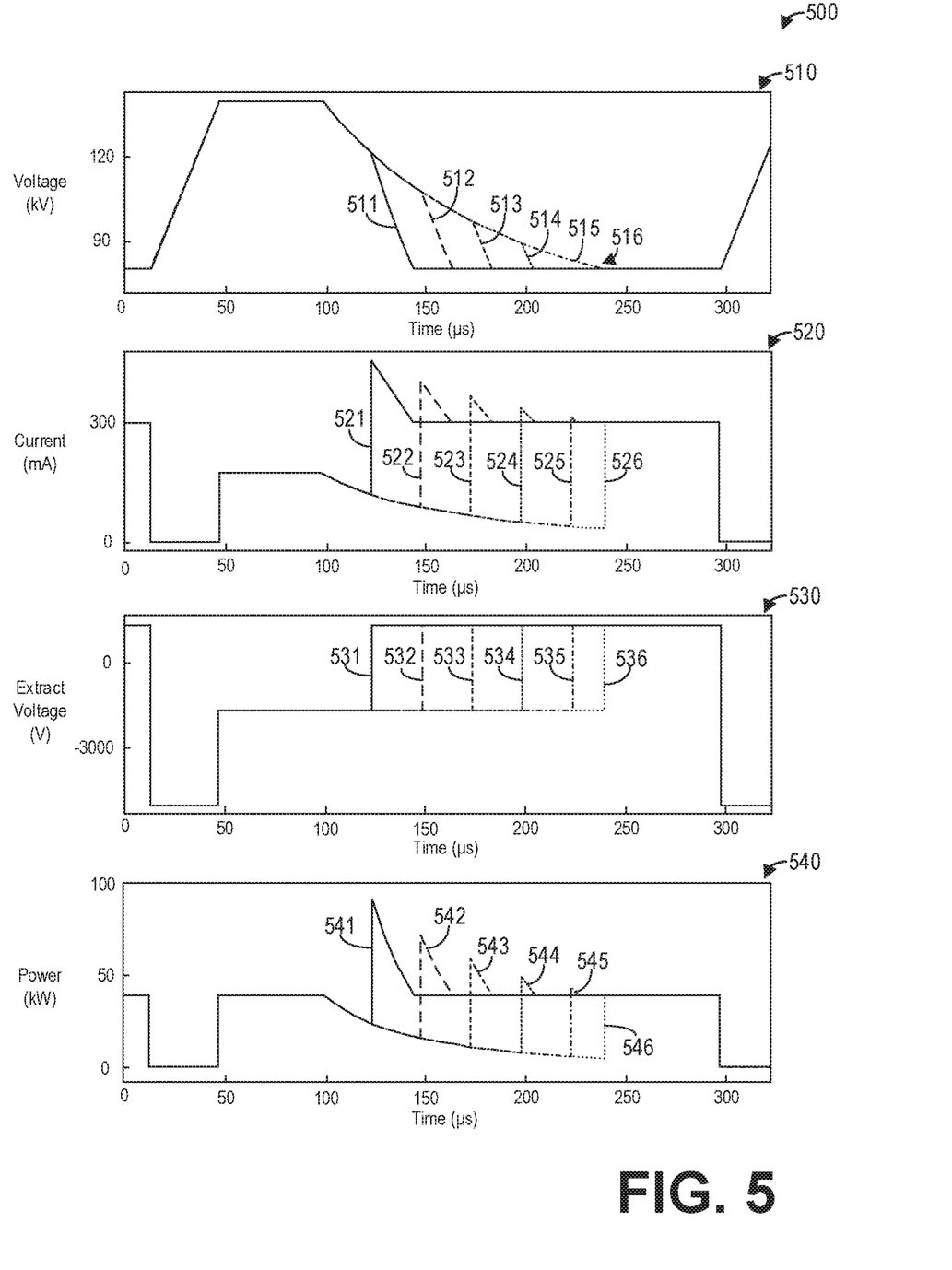
FIG. 5 shows a set of graphs illustrating x-ray generation parameters with a delay applied to an extraction voltage according to an embodiment.
Figure 6:
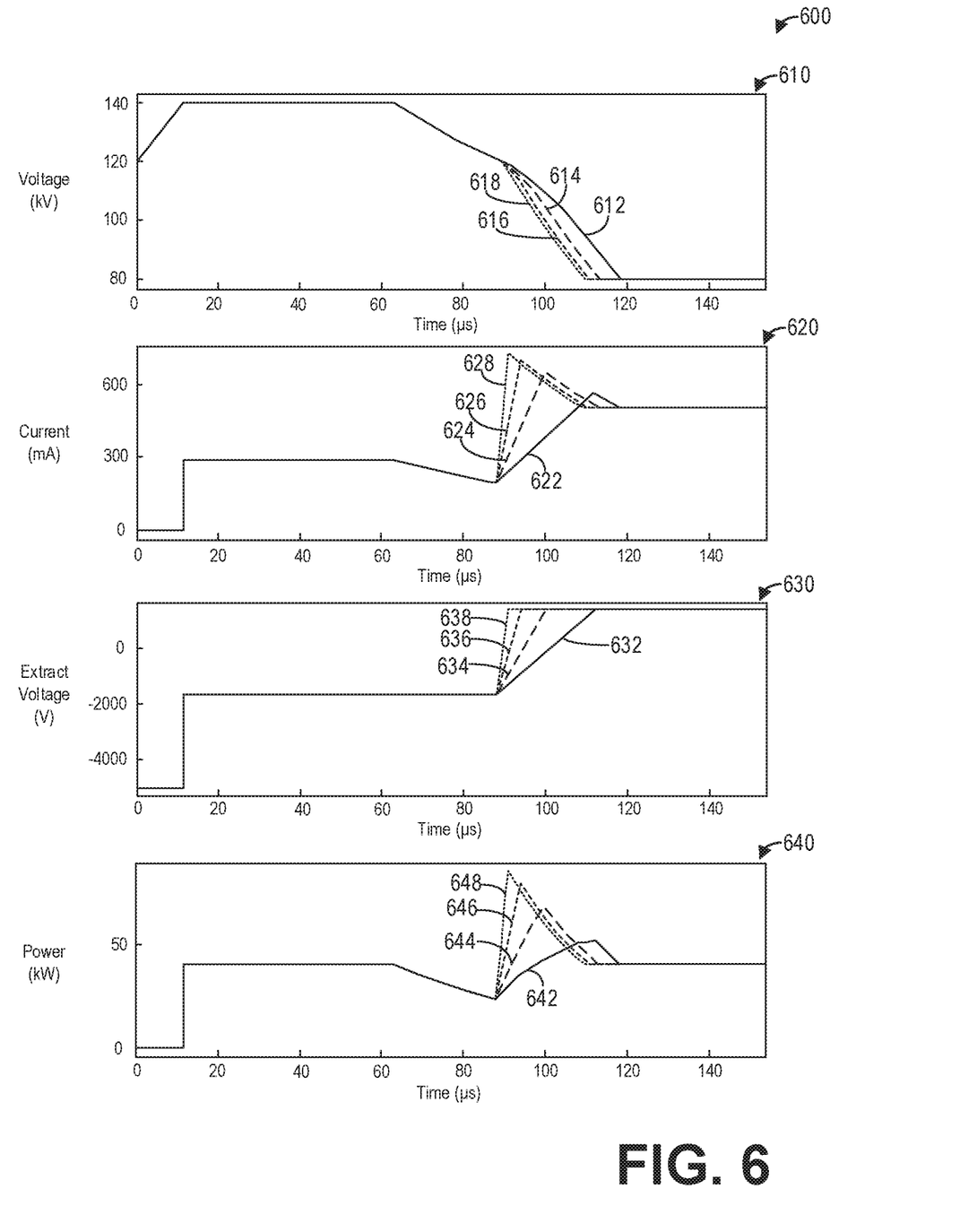
FIG. 6 shows a set of graphs illustrating example x-ray control parameters with a slope applied to an extraction voltage according to an embodiment.

The following description relates to various embodiments of medical imaging systems. In particular, systems and methods are provided for spectral energy imaging with computed tomography (CT) imaging systems. An example of a CT imaging system that may be used to acquire images in accordance with the present techniques is provided in FIGS. 1-3. For spectral energy or dual energy imaging with a CT imaging system, an x-ray source generates x-rays at a first energy and a second energy. To that end, the x-ray source is driven with a first, higher voltage to generate x-rays with the first energy and a second, lower voltage to generate x-rays with the second energy. While the transition from the lower voltage to the higher voltage simply includes increasing the tube voltage, the transition from the higher voltage to the lower voltage is constrained by a parasitic capacitor of a high-voltage cable providing the voltage to the x-ray source. Consequently, the transition duration of the kV fall or the transition from the higher voltage to the lower voltage may be slower than the transition from the lower voltage to the higher voltage, especially for lower output power as depicted in FIG. 4. A longer kV fall may negatively impact energy separation of acquired projection data, which in turn reduces the accuracy of basis material decomposition (BMD) as well as image quality of images reconstructed from the acquired projection data. One approach to reducing the kV fall transition time includes causing the tube current to peak during the transition, as depicted by FIGS. 5 and 6. A method for causing the tube current to peak during the transition, such as the method depicted in FIG. 7, includes selectively controlling the extract voltage applied to the cathode of the x-ray source. A method for dual energy imaging, such as the method depicted in FIG. 8, thus includes controlling the current of the x-ray source during the kV fall in order to reduce the transition time, thereby improving energy separation and image quality.

Figure 1:
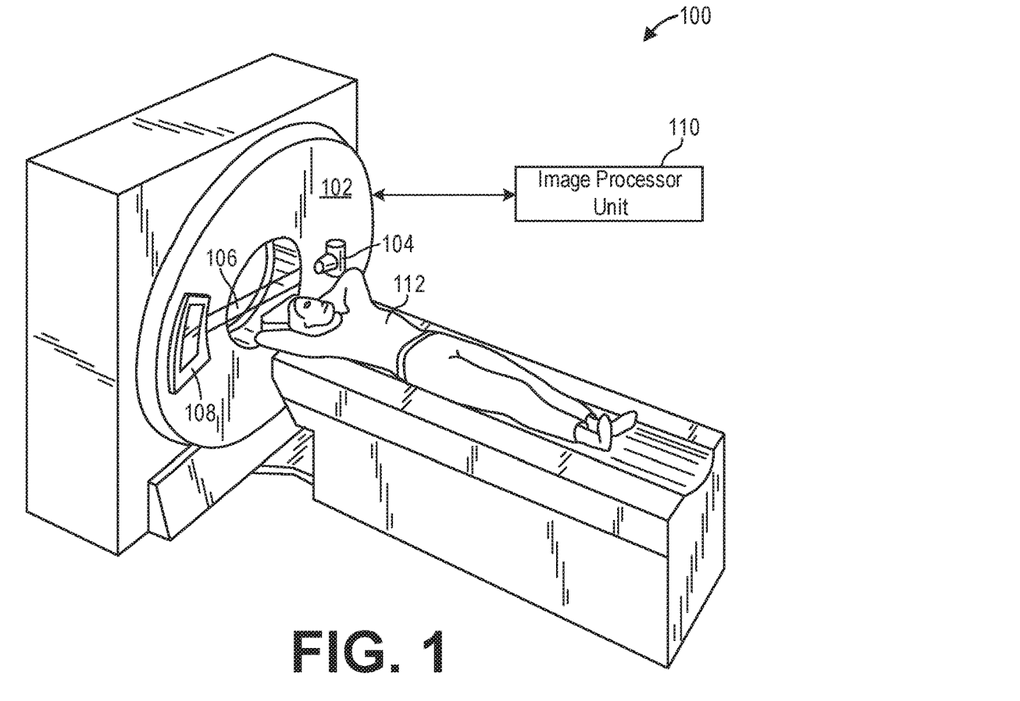
FIG. 1 shows a pictorial view of an imaging system according to an embodiment.

FIG. 1 illustrates an exemplary CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation 106 for use in imaging the subject 112. Specifically, the x-ray source 104 is configured to project the x-rays 106 towards a detector array 108 positioned on the opposite side of the gantry 102. Although FIG. 1 depicts only a single x-ray source 104, in certain embodiments, multiple x-ray radiation sources and detectors may be employed to project a plurality of x-rays 106 for acquiring projection data corresponding to the patient at different energy levels. In some embodiments, the x-ray source 104 may enable dual-energy gemstone spectral imaging (GSI) by rapid kVp switching. In some embodiments, the x-ray detector employed is a photon-counting detector which is capable of differentiating x-ray photons of different energies. In other embodiments, two sets of x-ray tube-detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered backprojection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some known CT imaging system configurations, a radiation source projects a cone-shaped beam which is collimated to lie within an X-Y-Z plane of a Cartesian coordinate system and generally referred to as an "imaging plane." The radiation beam passes through an object being imaged, such as the patient or subject 112. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view." A "scan" of the object includes a set of views made at different gantry angles, or view angles, during one revolution of the radiation source and detector. It is contemplated that the benefits of the methods described herein accrue to medical imaging modalities other than CT, so as used herein the term view is not limited to the use as described above with respect to projection data from one gantry angle. The term "view" is used to mean one data acquisition whenever there are multiple data acquisitions from different angles, whether from a CT, PET, or SPECT acquisition, and/or any other modality including modalities yet to be developed as well as combinations thereof in fused embodiments.

The projection data is processed to reconstruct an image that corresponds to a two-dimensional slice taken through the object. One method for reconstructing an image from a set of projection data is referred to in the art as the filtered backprojection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Figure 2:
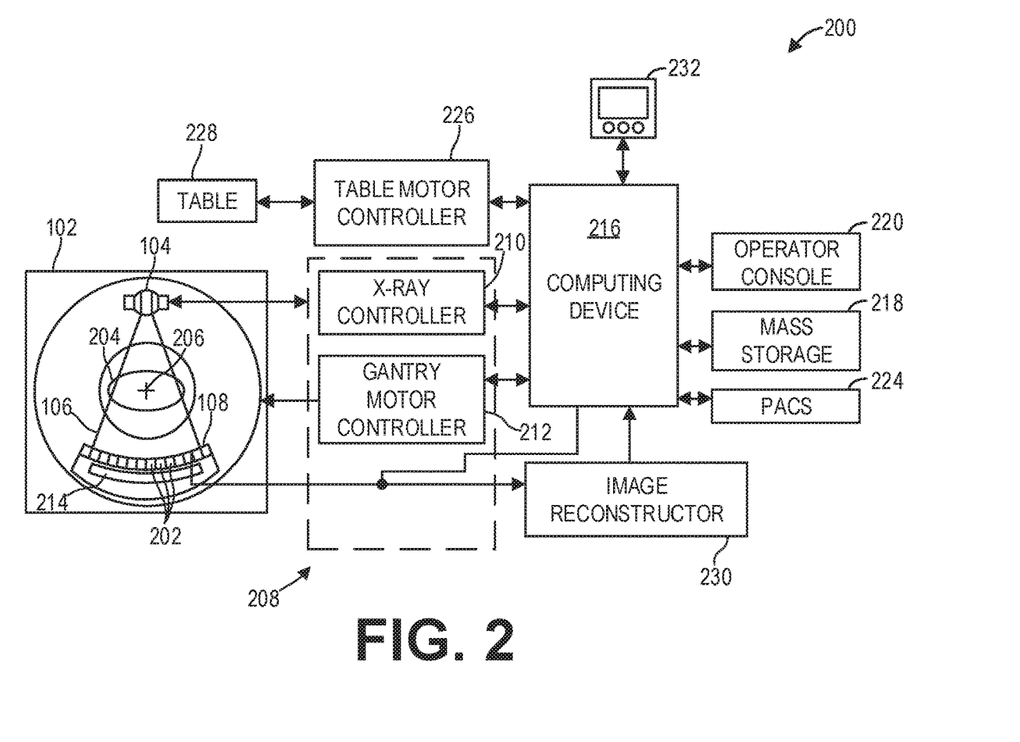
FIG. 2 shows a block schematic diagram of an exemplary imaging system according to an embodiment.

FIG. 2 illustrates an exemplary imaging system 200 similar to the CT system 100 of FIG. 1. In accordance with aspects of the present disclosure, the imaging system 200 is configured for imaging a subject 204. In one embodiment, the imaging system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may comprise photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of the two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the imaging system 200 either includes or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 228 which may comprise a motorized table. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

The various methods and processes described further herein may be stored as executable instructions in non-transitory memory on a computing device in imaging system 200. In one embodiment, image reconstructor 230 may include such executable instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

Figure 3:
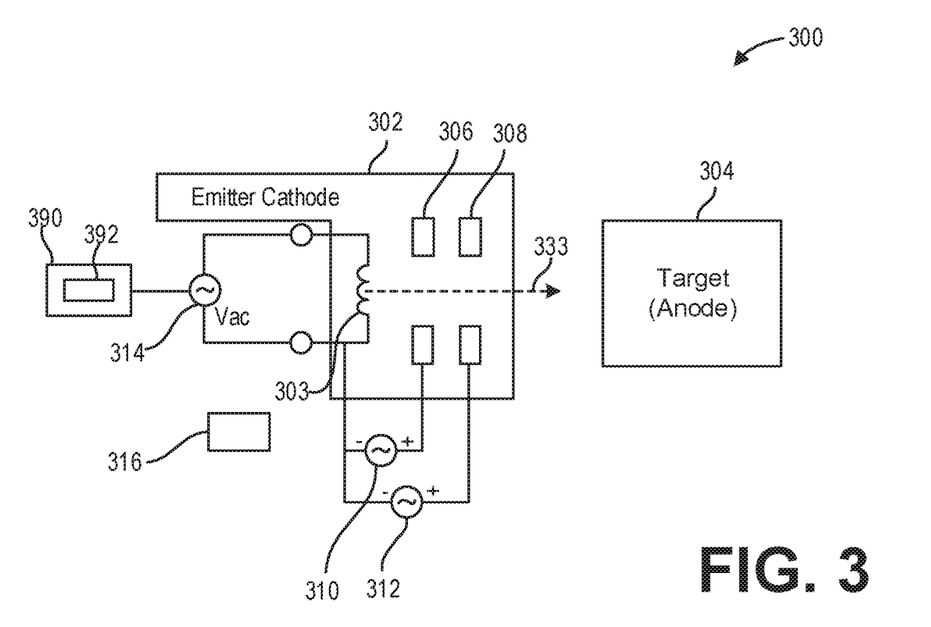
FIG. 3 shows a simplified block diagram of an example x-ray tube assembly according to an embodiment.

FIG. 3 shows a simplified block diagram of an x-ray tube assembly 300 formed in accordance with various embodiments. The x-ray tube assembly 300 may be provided, for example, as the x-ray source 104 in the CT system 100 or the imaging system 200. In the illustrated embodiment, the x-ray tube assembly 300 includes an emitter cathode structure 302 or cathode 302, which may comprise, but is not limited to a Pierce Gun, as well as a target 304 or anode 304. Both the cathode 302 and the anode 304 may be positioned in a housing or casing of the x-ray tube assembly 300. A voltage source 314 is provided in various embodiments that supplies a voltage to the emitter 303, which may then emit an electron beam 333 as a result of being heated by the current supplied by the voltage source 314. It should be noted that different elements may be used instead of the voltage source 314, such as a current source or an indirectly heated emitter, among others. The electron beam 333 may be directed towards the anode 304 to produce x-rays, for example, by accelerating the electron beam 333 from the emitter 303 towards the anode 304 by applying a potential difference between the cathode 302 and the anode 304. It should be noted that the anode 304 may be provided in different shapes and configurations.

The cathode 302 may further include an emitter focusing electrode 306, an extraction electrode 308, and optionally a downstream focusing electrode (not shown). In the illustrated embodiment, the emitter focusing electrode 306 is disposed proximate the emitter 303 and the extraction electrode 308 is disposed downstream of the emitter focusing electrode 306 and the emitter 303, and the downstream focusing electrode, if provided, is disposed downstream of the emitter focusing electrode 306, with the extraction electrode 308 thus interposed between the emitter focusing electrode 306 and the downstream focusing electrode. The electrodes may be provided with different geometries or arrangements, in different embodiments.

The voltage and current supplied to the emitter focusing electrode 306 and the extraction electrode 308 are controlled in accordance with various embodiments. In various embodiments, the voltage and/or current supplied to the emitter focusing electrode 306 and the extraction electrode 308 may be independently or separately controlled and allows for fast switching transitions or slow changing waveforms between different voltages. In the illustrated embodiment, a controller 316 is provided to control the voltage and/or current signals applied to the emitter focusing electrode 306 and the extraction electrode 308 by the voltage sources 310 and 312, respectively.

The transition from the higher voltage to the lower voltage is constrained by a parasitic capacitor 392 of a high-voltage cable 390 providing the voltage to the voltage source 314. As described further herein, the controller 316 may control an extract voltage applied by the voltage source 312 to the extraction electrode 308, for example, to reduce an amount of time to transition from a high tube voltage to a low tube voltage during dual energy imaging.

FIG. 4 shows a set of graphs 400 illustrating x-ray generation parameters for an extract sequence during dual energy imaging according to an embodiment. The set of graphs 400 includes a first graph 410 illustrating voltage, measured in kilovolts (kV), as a function of time, measured in microseconds (μs). The set of graphs 400 further includes a second graph 420 illustrating current, measured in milliamperes (mA), as a function of time, measured in microseconds. The set of graphs 400 further includes a third graph 430 illustrating extract voltage, measured in volts (V), as a function of time. The set of graphs 400 further includes a fourth graph 440 illustrating power, measured in kilowatts (kW), as a function of time.

The set of graphs 400 illustrate how the duration of a kV fall or transition from a high kV of 140 kV to a low kV of 80 kV changes for the different powers. To that end, each graph of the set of graphs 400 includes a plurality of plots corresponding to different powers.

For a power of 80 kW, the first graph 410 includes a plot 412 depicting the tube voltage over time, the second graph 420 includes a plot 422 depicting the tube current over time, the third graph 430 includes a plot 432 depicting the extract voltage over time, and the fourth graph 440 includes a plot 442 depicting the power over time.

For a power of 60 kW, the first graph 410 includes a plot 414 depicting the tube voltage over time, the second graph 420 includes a plot 424 depicting the tube current over time, the third graph 430 includes a plot 434 depicting the extract voltage over time, and the fourth graph 440 includes a plot 444 depicting the power over time.

For a power of 50 kW, the first graph 410 includes a plot 416 depicting the tube voltage over time, the second graph 420 includes a plot 426 depicting the tube current over time, the third graph 430 includes a plot 436 depicting the extract voltage over time, and the fourth graph 440 includes a plot 446 depicting the power over time.

For a power of 40 kW, the first graph 410 includes a plot 418 depicting the tube voltage over time, the second graph 420 includes a plot 428 depicting the tube current over time, the third graph 430 includes a plot 438 depicting the extract voltage over time, and the fourth graph 440 includes a plot 448 depicting the power over time.

Typically, the extract voltage is adjusted from a first extract voltage to a second extract voltage when the voltage reaches the second tube voltage or low kV, so that the current is driven to a current level corresponding to the tube current. For example, as depicted by plot 432, the extract voltage is increased from a first extract voltage level to a second extract voltage level when the tube voltage reaches the low kV, as depicted by plot 412. Increasing the extract voltage as depicted by plot 432 in turn causes the tube current to increase, as depicted by plot 422, to a selected tube current for the low kV. Increasing the extract voltage and thus the tube current further causes the power to return to the power level of 80 kW, as depicted by plot 442.

As depicted in the set of graphs 400, for lower powers, the current is lower and the duration of the kV fall is longer. For example, for a power of 80 kW, the duration of the kV fall is approximately 45 μs as depicted by plot 412, whereas for a power of 40 kW, the duration of the kV fall is approximately 135 μs as depicted by plot 418. Thus the extract voltage is adjusted at later times for lower powers, as depicted by the graph 430.

The duration of the kV fall or the transition from the high tube voltage to the low tube voltage determines the energy separation of projection data acquired during dual energy imaging, and thus impacts the image quality. For example, an increase in the duration of kV fall causes a decrease in the energy separation, and so the image quality may decrease. Conversely, a decrease in the duration of kV fall causes an increase in energy separation, and thus an increase in image quality.

While the transition from the low kV to the high kV may be relatively fast, the transition from the high kV to the low kV is restrained due to a parasitic capacitor in a high-voltage cable providing high voltage to the x-ray tube assembly 300, for example. The kV fall thus relates to the discharging of such a parasitic capacitor. The capacitor may be discharged more rapidly by flowing current through the high-voltage cable.

An x-ray tube assembly such as the x-ray tube assembly 300 enables a faster mA response in comparison to previous x-ray tube assemblies in CT imaging systems. For example, the x-ray tube assembly 300 provides current control that is 1,000 times faster than previous systems through the control of the extract voltage. For example, on previous x-ray tube assemblies, the response time for mA control was approximately 1 millisecond, whereas the response time for mA control with the x-ray tube assembly 300 is approximately 1 microsecond.

As the response time of the mA control for the x-ray tube assembly 300 is shorter than the transition duration of the kV fall, which may range from 45 microseconds to 135 microseconds in the depicted examples of FIG. 4, one approach to reducing the duration of the kV fall may include controlling the extract voltage to temporarily increase mA during the kV fall. That is, by temporarily increasing the tube current during the kV fall, the transition duration may be reduced.

One approach to temporarily increasing the tube current during the kV fall may include increasing the extract voltage during the kV transition rather than at the end of the kV transition. As an illustrative example, FIG. 5 shows a set of graphs 500 illustrating x-ray generation parameters with a delay applied to an extract voltage according to an embodiment. The set of graphs 500 includes a first graph 510 illustrating voltage, measured in kilovolts (kV), as a function of time, measured in microseconds ($\mu$s). The set of graphs 500 further includes a second graph 520 illustrating current, measured in milliamperes (mA), as a function of time, measured in microseconds. The set of graphs 500 further includes a third graph 530 illustrating extract voltage, measured in volts (V), as a function of time. The set of graphs 500 further includes a fourth graph 540 illustrating power, measured in kilowatts (kW), as a function of time.

The set of graphs 500 illustrate how the duration of a kV fall or transition from a high kV of 140 kV to a low kV of 80 kV changes for the different time delays added to the extract voltage. To that end, each graph of the set of graphs 400 includes a plurality of plots corresponding to different delays. In particular, the time delay of the extract voltage comprises a duration beginning at the kV fall or the transition from the high tube voltage to the low tube voltage. In other words, the time delay corresponds to an amount of time after the beginning of the kV fall when the extract voltage is controlled to a desired extract voltage for low tube voltage. The time delays depicted in the set of graphs 500 include time delays of 25 $\mu$s, 50 $\mu$s, 75 $\mu$s, 100 $\mu$s, 125 $\mu$s, and 150 $\mu$s, with a power of 40 kW for each of the different time delays.

For a delay of 25 $\mu$s, the first graph 510 includes a plot 511 of the tube voltage over time, the second graph 520 includes a plot 521 of the tube current over time, the third graph 530 includes a plot 531 of the extract voltage over time, and the fourth graph 540 includes a plot 541 of the power over time. As depicted, the voltage shown by plot 511 begins to fall or transition from the high voltage of 140 kV to the low voltage at approximately 100 $\mu$s, and the tube current and power shown by plots 521 and 541 respectively begin to fall as well. The extract voltage shown by plot 531 is controlled from a first extract voltage, maintained during the high kV transmission when the tube voltage is held at the high tube voltage of 140 kV, to a second extract voltage according to the time delay of 25 $\mu$s after the beginning of the kV fall. As a result, the tube current shown by plot 521 increases above a target tube current for the low tube voltage responsive to the extract voltage shifting to the second extract voltage, and then the tube current falls to the target tube current. A power peak depicted by the plot 541 occurs when the tube current peaks, but returns to the power of 40 kW when the tube current settles to the target tube current of 300 mA. Notably, the tube voltage begins to fall linearly, as depicted by plot 511, when the tube current peaks above the target tube current, such that the tube voltage reaches the low kV when the tube current settles to the target tube current as depicted by plot 521.

For a delay of 50 $\mu$s, the first graph 510 includes a plot 512 of the tube voltage over time, the second graph 520 includes a plot 522 of the tube current over time, the third graph 530 includes a plot 532 of the extract voltage over time, and the fourth graph 540 includes a plot 542 of the power over time. The extract voltage is adjusted to the second extract voltage 50 $\mu$s after the tube voltage begins to transition from the high kV to the low kV, as depicted by plots 512 and 532. As a result, the tube current peaks above the target tube current when the extract voltage shifts and then falls to the target tube current, as depicted by plot 522. The power similarly peaks due to the tube current peak, but returns to the power of 40 kW as depicted by plot 542. The tube voltage begins to transition linearly responsive to the tube current peak, as depicted by plot 512, and reaches the low kV at the same time that the tube current settles to the target tube current. Further, the current peak depicted by plot 522 and the power peak depicted by plot 542 are lower than the current peak and power peak depicted by plots 521 and 541, respectively.

Similar reductions in the transition time for the tube voltage are achieved for longer delays. For example, for a delay of 75 $\mu$s, the first graph 510 includes a plot 513 of the tube voltage over time, the second graph 520 includes a plot 523 of the tube current over time, the third graph 530 includes a plot 533 of the extract voltage over time, and the fourth graph 540 includes a plot 543 of the power over time. For a delay of 100 $\mu$s, the first graph 510 includes a plot 514 of the tube voltage over time, the second graph 520 includes a plot 524 of the tube current over time, the third graph 530 includes a plot 534 of the extract voltage over time, and the fourth graph 540 includes a plot 544 of the power over time. For a delay of 125 $\mu$s, the first graph 510 includes a plot 515 of the tube voltage over time, the second graph 520 includes a plot 525 of the tube current over time, the third graph 530 includes a plot 535 of the extract voltage over time, and the fourth graph 540 includes a plot 545 of the power over time. For a delay of 150 $\mu$s, the first graph 510 includes a plot 516 of the tube voltage over time, the second graph 520 includes a plot 526 of the tube current over time, the third graph 530 includes a plot 536 of the extract voltage over time, and the fourth graph 540 includes a plot 546 of the power over time.

It should be appreciated that as the tube voltage reaches the low kV after 135 $\mu$s, as discussed hereinabove with regard to FIG. 4, the delay of 150 $\mu$s applied to the extract voltage as depicted by plot 536 does not result in a peak in tube current or power, as depicted by plots 526 and 546, and clearly does not cause a reduction in transition time for the kV fall. Similarly, while the delay of 125 $\mu$s applied to the extract voltage as depicted by plot 535 results in a small peak in tube current and power, as depicted by plots 525 and 545, there is no substantial reduction in transition time for the kV fall as depicted by plot 515.

Thus, a reduction in kV fall duration may be achieved by shifting the extract voltage during the kV fall so that the tube current temporarily peaks above a target tube current. The shorter the delay, or more specifically the duration between the start of the kV fall and the shift in extract voltage, the shorter the kV fall duration overall. The particular delay selected for applying to the extract voltage depends on dose limits, which may constrain permissible peaks in power.

Another approach to reducing the kV fall transition duration includes gradually increasing the extract voltage during the kV fall. As an illustrative example, FIG. 6 shows a set of graphs 600 illustrating example x-ray generation parameters with a slope applied to the extract voltage according to an embodiment. The set of graphs 600 includes a first graph 610 illustrating voltage, measured in kilovolts (kV), as a function of time, measured in microseconds (µs). The set of graphs 600 further includes a second graph 620 illustrating current, measured in milliamperes (mA), as a function of time, measured in microseconds. The set of graphs 600 further includes a third graph 630 illustrating extract voltage, measured in volts (V), as a function of time. The set of graphs 600 further includes a fourth graph 640 illustrating power, measured in kilowatts (kW), as a function of time.

The set of graphs 600 illustrate how the duration of a kV fall or transition from a high kV of 140 kV to a low kV of 80 kV changes for the different slopes in the transition of the extract voltage from a first extract voltage, corresponding to an extract voltage for the high tube voltage, to a second extract voltage, corresponding to an extract voltage for the low tube voltage. To that end, each graph of the set of graphs 400 includes a plurality of plots corresponding to different transition slopes for the extract voltage. In particular, the slopes of the extract voltage comprise temporal slopes or changes in the extract voltage over time. The extract voltage begins the sloped transition prior to the tube voltage reaching the low tube voltage, and may be determined according to a desired kV fall duration. In the depicted examples, the extract voltage begins to transition when the tube voltage falls to 120 kV. The temporal slopes depicted in the set of graphs 600 include slopes of 125 volts per microsecond (V/µs), 250 V/µs, 500 V/αs, and 1000 V/µs, with a power of 40 kW for each example.

For a slope of 125 V/µs, the first graph 610 includes a plot 612 of the tube voltage over time, the second graph 620 includes a plot 622 of the tube current over time, the third graph 630 includes a plot 632 of the extract voltage over time, and the fourth graph 640 includes a plot 642 of the power over time. As depicted by the plot 632, the extract voltage is initially maintained at a first extract voltage during the kV fall, and then increases at a rate of 125 V/µs to a second extract voltage. In turn, the tube current gradually increases and peaks above a target tube current before settling down to the target tube current, as depicted by plot 622, which causes a corresponding gradual increase and peak in power as depicted by plot 642. Notably, the tube current initially falls or decreases from a first tube current along with the tube voltage during the kV fall, as depicted by plot 622. Further, the tube voltage begins to decrease faster toward the low kV, as depicted by plot 612, when the tube current increases above the first tube current. The tube voltage reaches the low kV when the tube current settles to the target tube current after peaking, as depicted by plots 612 and 622 respectively.

Higher slopes in the extract voltage result in higher tube current and power peaks, as well as shorter kV fall durations overall. For a slope of 250 V/µs, the first graph 610 includes a plot 614 of the tube voltage over time, the second graph 620 includes a plot 624 of the tube current over time, the third graph 630 includes a plot 634 of the extract voltage over time, and the fourth graph 640 includes a plot 644 of the power over time. For a slope of 500 V/µs, the first graph 610 includes a plot 616 of the tube voltage over time, the second graph 620 includes a plot 626 of the tube current over time, the third graph 630 includes a plot 636 of the extract voltage over time, and the fourth graph 640 includes a plot 646 of the power over time. For a slope of 1000 V/µs, the first graph 610 includes a plot 618 of the tube voltage over time, the second graph 620 includes a plot 628 of the tube current over time, the third graph 630 includes a plot 638 of the extract voltage over time, and the fourth graph 640 includes a plot 648 of the power over time.

Doubling the slope in extract voltage from 125 V/µs to 250 V/µs results in a larger reduction in kV fall duration than doubling the slope from 500 V/µs to 1000 V/µs. Consequently, a lower slope closer to 250 V/µs may be preferable to a slope of 1000 V/µs, especially when considering the relatively higher peak in power as depicted by the plots 644 and 648.

Thus, controlling the extract voltage from a first extract voltage to a second extract voltage during a kV fall of a tube voltage causes a reduction in duration of the kV fall. The extract voltage may be increased instantaneously from the first extract voltage to the second extract voltage, as depicted in FIG. 5, in some examples. In other examples, the extract voltage may be increased gradually from the first extract voltage to the second extract voltage, as depicted in FIG. 6. In other examples, a combination of gradually increasing the extract voltage, as depicted in FIG. 6, along with adjusting the timing of the increase, as depicted in FIG. 5, may be used to reduce the duration of the kV fall while constraining a resulting peak in output power.

Figure 7:
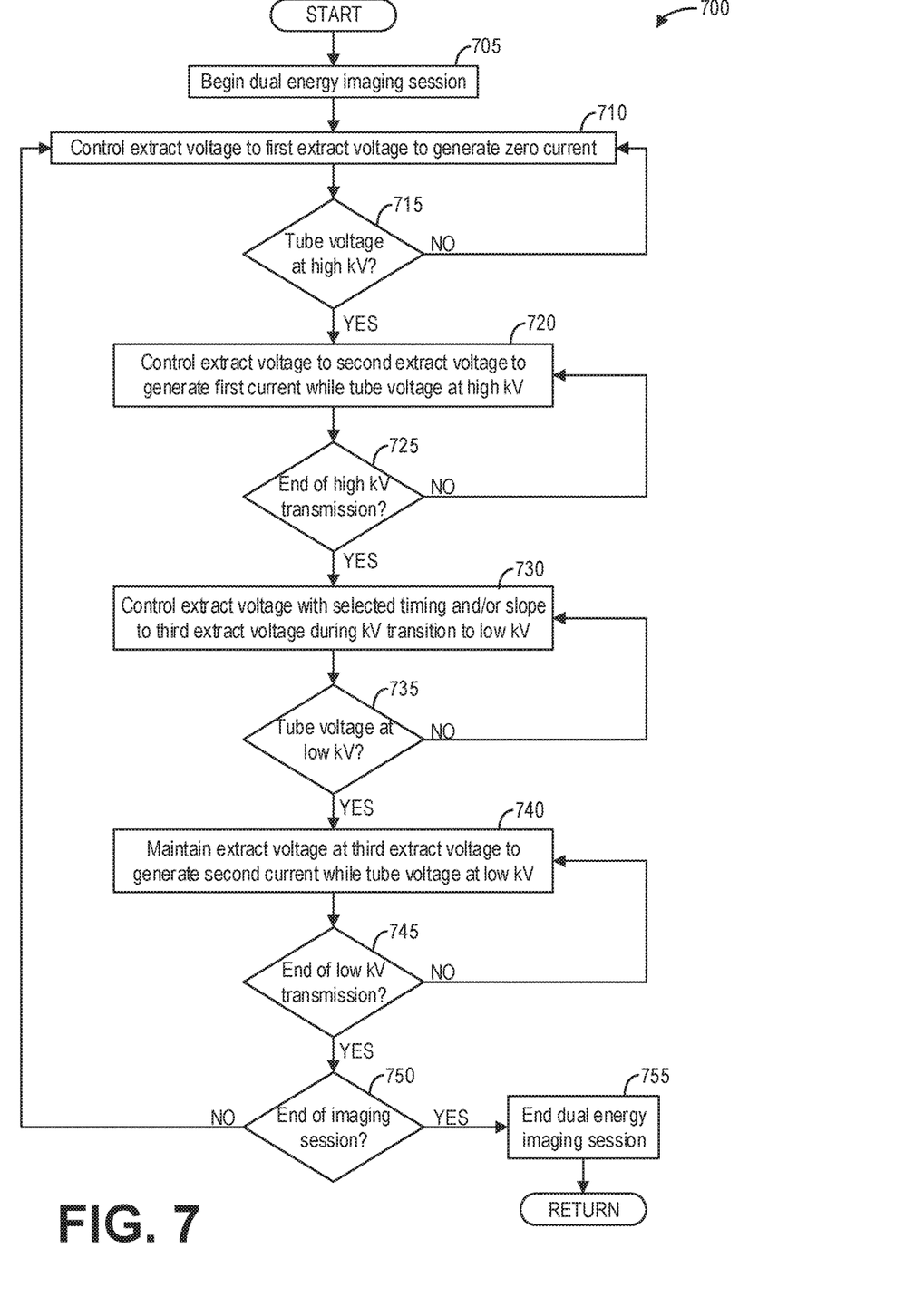
FIG. 7 shows a high-level flow chart illustrating an example method for controlling an extract voltage of an x-ray tube apparatus according to an embodiment.

FIG. 7 shows a high-level flow chart illustrating an example method 700 for controlling an extract voltage of an x-ray tube apparatus according to an embodiment. In particular, method 700 relates to controlling an extract voltage to reduce a transition duration of an x-ray tube voltage from a high energy or high kV transitioning to a low energy or low kV. Method 700 is described with regard to the systems and components of FIGS. 1-3, though it should be appreciated that the method 700 may be implemented with other systems and components without departing from the scope of the present disclosure. Method 700 may be implemented as instructions in non-transitory memory and executable by a processor, such as the memory and processor of the computing device 216 of the imaging system 200.

Method 700 begins at 705. At 705, method 700 begins a dual energy imaging session. During the dual energy imaging session, method 700 controls the x-ray source 104 to image the subject 204 with x-rays of two different energy levels. As discussed hereinabove, method 700 further detects the x-rays via the detector array 108 and reconstructs one or more images. By imaging the subject 204 with dual energies, the one or more images may comprise basis material images depicting the densities of basis materials within the subject. To that end, at the beginning of the dual energy imaging session, method 700 may initially control the x-ray source 104 with a first tube voltage or a high kV and a corresponding first tube current to generate higher energy x-rays.

Continuing at 710, method 700 controls the extract voltage to a first extract voltage to generate zero current while the tube voltage of the x-ray source is adjusted to the first tube voltage or the high kV. As an illustrative example, the graph 510 of FIG. 5 depicts the tube voltage being controlled to a high kV of 140 kV from approximately 10 µs to almost 50 µs. During this transition, the extract voltage is controlled to a first extract voltage, as depicted by graph 530, such that the current depicted by the graph 520 is maintained at zero mA. As the current is at zero mA, the x-ray source does not generate any x-rays during this transition.

Continuing at 715, method 700 determines whether the tube voltage has reached the first tube voltage or the high kV. If the tube voltage has not reached the high kV ("NO"), method 700 continues controlling the extract voltage to the first extract voltage.

Once the tube voltage has reached the high kV ("YES") at 715, method 700 continues to 720. At 720, method 700 controls the extract voltage to a second extract voltage to generate a first tube current while the tube voltage is at the high kV. Consequently, the x-ray source or x-ray tube generates an x-ray beam according to the first tube current and the first tube voltage. Referring again to the examples depicted in FIG. 5, the extract voltage is controlled to the second extract voltage of approximately −1500 V, as depicted by graph 530, when the tube voltage reaches the high kV of 140 kV, as depicted by graph 510, such that the tube current reaches the first tube current of approximately 200 mA, as depicted by graph 520.

At 725, method 700 determines if the high kV transmission has ended. The high kV transmission ends when the tube voltage begins to transition to a lower tube voltage. As an illustrative and non-limiting example, the high kV transmission may be configured with a threshold duration such that the tube voltage is controlled to a lower kV once the threshold duration elapses. Additionally or alternatively, the high kV transmission may be configured with a duration such that sufficient high kV transmission occurs for a given view. As such, the duration may be predetermined or determined dynamically based on gantry rotation speed, imaging objective, and so on. If the high kV transmission has not ended ("NO"), method 700 maintains the extract voltage at the second extract voltage at 720 while the high kV x-ray transmission continues.

Once the high kV transmission ends ("YES") at 725, method 700 continues to 730. At 730, method 700 controls the extract voltage with a selected timing and/or slope to a third extract voltage during the kV transition of the tube voltage from the high kV to a second tube voltage or low kV. In particular, method 700 controls the extract voltage such that the tube current spikes or peaks above a second tube current for the second tube voltage while the tube voltage is transitioning to the second tube voltage. To that end, method 700 may control the extract voltage to the third extract voltage with a selected timing or time delay, so that the extract voltage shifts instantaneously to the third extract voltage at a given time after the beginning of the tube voltage transition as described hereinabove with regard to FIG. 5, with a selected slope or rate of change in the extract voltage, so that the extract voltage gradually increases to the third extract voltage as described hereinabove with regard to FIG. 6, or with a combination of a selected time delay and a selected slope, so that the extract voltage begins to gradually increase to the third extract voltage after a selected time during the kV transition. The selection of the time delay and/or slope may depend on a desired power output, as shorter time delays and higher slopes result in substantially higher power peaks. In other examples, the selection of the time delay and/or slope may depend on a desired duration of the kV transition from the high tube voltage to the low tube voltage. For example, a particular duration of the kV transition may be desired to improve the energy separation for dual energy imaging.

At 735, method 700 determines if the tube voltage has reached the second tube voltage or the low kV. If the tube voltage has not reached the low kV ("NO"), method 700 continues controlling the extract voltage with the selected timing and/or slope to the third extract voltage. As discussed hereinabove with regard to FIGS. 5 and 6, the control of the extract voltage causes a peak in tube current during the kV transition, which in turn enables the tube voltage to transition to the low kV faster. In particular, the tube voltage reaches the low kV at substantially a same time that the tube current settles to the target tube current or second tube current after peaking, as depicted in FIGS. 5 and 6.

Once the tube voltage reaches the low kV ("YES"), method 700 continues to 740. At 740, method 700 maintains the extract voltage at the third extract voltage to maintain the tube current at the second tube current while the tube voltage is at the second tube voltage or low kV. While the extract voltage is maintained at the third extract voltage, the x-ray source or x-ray tube generates an x-ray beam according to the second tube current and the second tube voltage.

Continuing at 745, method 700 determines whether the low kV transmission has ended. The duration of the low kV transmission may depend, for example, on one or more of the gantry rotation speed, the imaging objective, a desired image quality, a desired dose level, and so on. If the low kV transmission has not ended ("NO"), method 700 maintains the extract voltage at the third extract voltage at 740.

Once the low kV transmission ends ("YES"), method 700 continues to 750. At 750, method 700 determines whether the imaging session is ending. The imaging session ends when the scan is complete, which may occur when a predetermined number of views are acquired at the dual energies across a given length of the subject, as a non-limiting and illustrative example. The imaging session may end when the scan is incomplete, for example in response to a user-input command to end the imaging session or responsive to detecting an issue with the imaging session.

If the imaging session is not ending ("NO"), method 700 returns to 710 to control the extract voltage to the first extract voltage such that the tube current is zero while the tube voltage is controlled to the first tube voltage or the high kV. Thus method 700 continues to control the extract voltage as discussed hereinabove to reduce the duration of the kV fall or the duration of the tube voltage transition from a high tube voltage to a low tube voltage. Once the imaging session ends ("YES") at 750, method 700 ends the dual energy imaging session at 755. Method 700 then returns.

Thus, a method for controlling the extract voltage of an x-ray source is provided that enables a reduction in tube voltage transition times. As a result of the reduction in tube voltage transition times, energy separation of projection data may be improved, thereby improving image quality.

Figure 8:
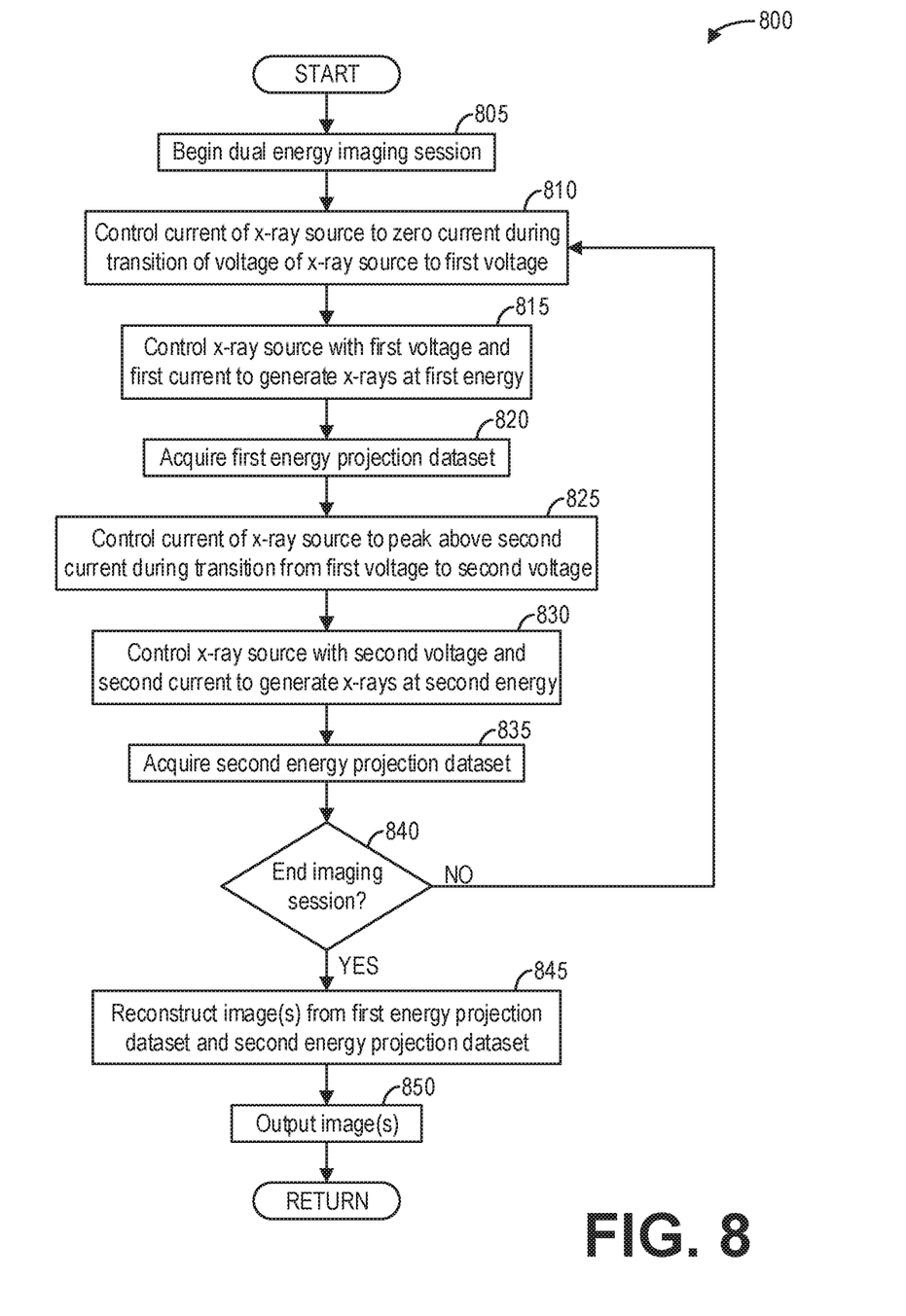
FIG. 8 shows a high-level flow chart illustrating an example method for dual energy imaging according to an embodiment.

While FIG. 7 is directed to controlling the extract voltage applied to the cathode of an x-ray source, it should be appreciated that the advantage of reducing the kV fall transition time may be obtained in general by selectively controlling the current during the transition. As an illustrative example, FIG. 8 shows a high-level flow chart illustrating an example method 800 for dual energy imaging according to an embodiment. Method 800 is described with regard to the systems and components of FIGS. 1-3, though it should be appreciated that method 800 may be implemented with other systems and components without departing from the scope of the present disclosure.

Method 800 begins at 805. At 805, method 800 begins a dual energy imaging session of a subject. At 810, method 800 controls the current of an x-ray source to zero during the transition of the tube voltage of the x-ray source to a first voltage, wherein the first voltage comprises a high tube voltage or high kV for the dual energy imaging session. At 815, method 800 controls the x-ray source with the first voltage and a first current to generate a first beam of x-rays with a first energy. At 820, method 800 acquires a first energy projection dataset. For example, method 800 detects the first beam of x-rays attenuated by the subject to acquire the first energy projection dataset. Continuing at 825, method 800 controls the current of the x-ray source to peak above a second current during the transition of the x-ray source voltage from the first voltage to a second voltage lower than the first voltage, wherein the second voltage comprises a low tube voltage or low kV. For example, method 800 may control the extract voltage as described hereinabove such that the current of the x-ray source increases above the second current, which in turn causes the tube voltage to decrease more rapidly to the second voltage. In other examples, method 800 may otherwise control the current to increase and peak above the second current to cause the voltage transition in accelerate. Once the tube voltage reaches the second voltage, method 800 continues to 830. At 830, method 800 controls the x-ray source with the second voltage and the second current to generate a second beam of x-rays with a second energy lower than the first energy. At 835, method 800 acquires a second energy projection dataset based on the second beam of x-rays. For example, method 800 detects the second beam of x-rays attenuated by the subject to acquire the second energy projection dataset. At 840, method 800 determines if the imaging session is ending. If the imaging session is not ending ("NO"), method 800 returns to 810 continue dual energy imaging of the subject by acquiring additional projection data for the first energy projection dataset and the second energy projection dataset. Once the imaging session is ended ("YES"), method 800 continues to 845. At 845, method 800 reconstructs one or more images from the first energy projection dataset and the second energy projection dataset. For example, method may perform basis material decomposition with the first energy projection dataset and the second energy projection dataset to generate basis material images as described hereinabove, and furthermore may reconstruct an additional image from the projection datasets and/or the basis material images. At 850, method 800 outputs the one or more images. For example, method 800 may output the one or more images to a display device, such as display device 232, for display to a user. Additionally or alternatively, method 800 may output the one or more images to a PACS 224 for remote review or to mass storage 218 for later retrieval. Method 800 then returns.

A technical effect of the disclosure includes controlling a tube current of an x-ray source to peak above a target current level during a transition of the x-ray source from a higher tube voltage to a lower tube voltage. Another technical effect of the disclosure includes a reduced transition time of an x-ray source from a higher tube voltage to a lower tube voltage. Yet another technical effect of the disclosure includes the improvement of energy separation in dual energy projection data. Another technical effect of the disclosure includes an improved image quality for basis material images.

In one embodiment, a method comprises controlling an x-ray source with a first voltage to generate x-rays at a first energy, controlling the x-ray source with a second voltage to generate x-rays at a second energy lower than the first energy, and controlling a current of the x-ray source to peak above a target current when a voltage of the x-ray source is transitioning from the first voltage to the second voltage.

In a first example of the method, controlling the current of the x-ray source to peak above the target current when the voltage of the x-ray source is transitioning comprises instantaneously increasing the current to a current level above the target current at a predetermined time after the tube voltage begins transitioning from the first voltage to the second voltage. In a second example of the method optionally including the first example, controlling the current of the x-ray source to peak above the target current when the voltage of the x-ray source is transitioning comprises gradually increasing the current to a current level above the target current while the tube voltage is transitioning from the first voltage to the second voltage. In a third example of the method optionally including one or more of the first and second examples, controlling the current of the x-ray source to peak above the target current when the voltage of the x-ray source is transitioning comprises gradually increasing the current, responsive to a predetermine time elapsing after the tube voltage begins transitioning, to a current level above the target current while the tube voltage is transitioning from the first voltage to the second voltage. In a fourth example of the method optionally including one or more of the first through third examples, controlling the current of the x-ray source to peak above the target current comprises controlling an extract voltage applied to a cathode of the x-ray source from a first extract voltage to a second extract voltage to cause the current of the x-ray source to peak above the target current. In a fifth example of the method optionally including one or more of the first through fourth examples, controlling the extract voltage comprises increasing the extract voltage from the first extract voltage to the second extract voltage at a predetermined time while the voltage of the x-ray source is transitioning. In a sixth example of the method optionally including one or more of the first through fifth examples, controlling the extract voltage comprises gradually increasing the extract voltage at a predetermined rate of change from the first extract voltage to the second extract voltage while the voltage of the x-ray source is transitioning. In a seventh example of the method optionally including one or more of the first through sixth examples, the method further comprises controlling the current to zero current when the voltage is transitioning from the second voltage to the first voltage. In an eighth example of the method optionally including one or more of the first through seventh examples, the method further comprises reconstructing at least one image of a subject from projection data, the projection data corresponding to the x-rays attenuated by the subject and detected by an x-ray detector.

In another embodiment, a method for dual energy imaging comprises controlling an x-ray source with a first voltage and a first current to generate x-rays with a first energy, controlling the x-ray source with a second voltage and a second current to generate x-rays with a second energy lower than the first energy, and controlling an extract voltage of a cathode of the x-ray source to cause a current of the x-ray source to peak above the second current when a voltage of the x-ray source is transitioning from the first voltage to the second voltage.

In a first example of the method, the method further comprises maintaining the extract voltage at a first extract voltage when the voltage of the x-ray source is maintained at the first voltage, and maintaining the extract voltage at a second extract voltage when the voltage of the x-ray source is maintained at the second voltage. In a second example of the method optionally including the first example, controlling the extract voltage to cause the current of the x-ray source to peak above the second current comprises increasing the extract voltage to the second extract voltage at a predetermined time after the voltage of the x-ray source begins transitioning from the first voltage to the second voltage. In a third example of the method optionally including one or more of the first and second examples, controlling the extract voltage to cause the current of the x-ray source to peak above the second current comprises gradually increasing the extract voltage to the second extract voltage at a predetermined rate while the voltage of the x-ray source is between the first voltage and the second voltage. In a fourth example of the method optionally including one or more of the first through third examples, controlling the extract voltage to cause the current of the x-ray source to peak above the second current comprises controlling the extract voltage to gradually increase, beginning at a predetermined time after the voltage of the x-ray source begins transitioning to the second voltage, to the second extract voltage at a predetermined rate.

In yet another embodiment, a system comprises an x-ray source that emits, towards a subject to be imaged, a first beam of x-rays with a first energy and a second beam of x-rays with a second energy lower than the first energy, a detector configured to receive x-rays attenuated by the subject, a data acquisition system (DAS) operably connected to the detector, and a computing device operably connected to the DAS and configured with executable instructions in non-transitory memory that when executed cause the computing device to: control the x-ray source with a first tube voltage to generate the first beam of x-rays, control the x-ray source with a second tube voltage to generate the second beam of x-rays, and control a current of the x-ray source to peak above a target current when a voltage of the x-ray source is transitioning from the first voltage to the second voltage.

In a first example of the system, the x-ray source comprises a cathode and an anode, and the computing device is further configured with executable instructions in non-transitory memory that when executed cause the computing device to control the current of the x-ray source by controlling an extract voltage applied to the cathode such that the current of the x-ray source peaks above the target current when the voltage of the x-ray source is transitioning from the first voltage to the second voltage. In a second example of the system optionally including the first example, controlling the extract voltage applied to the cathode such that the current of the x-ray source peaks above the target current comprises increasing the extract voltage from a first extract voltage to a second extract voltage at a predetermined time after the voltage of the x-ray source begins transitioning from the first voltage to the second voltage. In a third example of the system optionally including one or more of the first and second examples, controlling the extract voltage applied to the cathode such that the current of the x-ray source peaks above the target current comprises gradually increasing the extract voltage from a first extract voltage to a second extract voltage at a predetermined rate while the voltage of the x-ray source is between the first voltage and the second voltage. In a fourth example of the system optionally including one or more of the first through third examples, the computing device is further configured with executable instructions in non-transitory memory that when executed cause the computing device to control the current to zero current when the voltage is transitioning from the second voltage to the first voltage. In a fifth example of the system optionally including one or more of the first through fourth examples, the computing device is further configured with executable instructions in non-transitory memory that when executed cause the computing device to receive, via the DAS, projection data for both the first beam of x-rays and the second beam of x-rays, and reconstruct an image from the projection data.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. Although the examples provided herein are related to medical application, the scope of the present disclosure covers non-destructive testing in industrial, biomedical, and other fields. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
controlling an x-ray source with a first voltage to generate x-rays at a first energy;
controlling the x-ray source with a second voltage to generate x-rays at a second energy lower than the first energy; and
controlling a current of the x-ray source to peak above a target current when a voltage of the x-ray source is transitioning from the first voltage to the second voltage.

2. The method of claim 1, wherein controlling the current of the x-ray source to peak above the target current when the voltage of the x-ray source is transitioning comprises instantaneously increasing the current to a current level above the target current at a predetermined time after the tube voltage begins transitioning from the first voltage to the second voltage.

3. The method of claim 1, wherein controlling the current of the x-ray source to peak above the target current when the voltage of the x-ray source is transitioning comprises gradually increasing the current to a current level above the target current while the tube voltage is transitioning from the first voltage to the second voltage.

4. The method of claim 1, wherein controlling the current of the x-ray source to peak above the target current when the voltage of the x-ray source is transitioning comprises gradually increasing the current, responsive to a predetermine time elapsing after the tube voltage begins transitioning, to a current level above the target current while the tube voltage is transitioning from the first voltage to the second voltage.

5. The method of claim 1, wherein controlling the current of the x-ray source to peak above the target current comprises controlling an extract voltage applied to a cathode of the x-ray source from a first extract voltage to a second extract voltage to cause the current of the x-ray source to peak above the target current.

6. The method of claim 5, wherein controlling the extract voltage comprises increasing the extract voltage from the first extract voltage to the second extract voltage at a predetermined time while the voltage of the x-ray source is transitioning.

7. The method of claim 5, wherein controlling the extract voltage comprises gradually increasing the extract voltage at a predetermined rate of change from the first extract voltage to the second extract voltage while the voltage of the x-ray source is transitioning.

8. The method of claim 1, further comprising controlling the current to zero current when the voltage is transitioning from the second voltage to the first voltage.

9. The method of claim 1, further comprising reconstructing at least one image of a subject from projection data, the projection data corresponding to the x-rays attenuated by the subject and detected by an x-ray detector.

10. A method for dual energy imaging, comprising:
controlling an x-ray source with a first voltage and a first current to generate x-rays with a first energy;
controlling the x-ray source with a second voltage and a second current to generate x-rays with a second energy lower than the first energy; and
controlling an extract voltage of a cathode of the x-ray source to cause a current of the x-ray source to peak above the second current when a voltage of the x-ray source is transitioning from the first voltage to the second voltage.

11. The method of claim 10, further comprising maintaining the extract voltage at a first extract voltage when the voltage of the x-ray source is maintained at the first voltage, and maintaining the extract voltage at a second extract voltage when the voltage of the x-ray source is maintained at the second voltage.

12. The method of claim 11, wherein controlling the extract voltage to cause the current of the x-ray source to peak above the second current comprises increasing the extract voltage to the second extract voltage at a predetermined time after the voltage of the x-ray source begins transitioning from the first voltage to the second voltage.

13. The method of claim 11, wherein controlling the extract voltage to cause the current of the x-ray source to peak above the second current comprises gradually increasing the extract voltage to the second extract voltage at a predetermined rate while the voltage of the x-ray source is between the first voltage and the second voltage.

14. The method of claim 11, wherein controlling the extract voltage to cause the current of the x-ray source to peak above the second current comprises controlling the extract voltage to gradually increase, beginning at a predetermined time after the voltage of the x-ray source begins transitioning to the second voltage, to the second extract voltage at a predetermined rate.

15. A system, comprising:
an x-ray source that emits, towards a subject to be imaged, a first beam of x-rays with a first energy and a second beam of x-rays with a second energy lower than the first energy;
a detector configured to receive x-rays attenuated by the subject;
a data acquisition system (DAS) operably connected to the detector; and
a computing device operably connected to the DAS and configured with executable instructions in non-transitory memory that when executed cause the computing device to:
control the x-ray source with a first tube voltage to generate the first beam of x-rays;
control the x-ray source with a second tube voltage to generate the second beam of x-rays; and
control a current of the x-ray source to peak above a target current when a voltage of the x-ray source is transitioning from the first voltage to the second voltage.

16. The system of claim 15, wherein the x-ray source comprises a cathode and an anode, wherein the computing device is further configured with executable instructions in non-transitory memory that when executed cause the computing device to control the current of the x-ray source by controlling an extract voltage applied to the cathode such that the current of the x-ray source peaks above the target current when the voltage of the x-ray source is transitioning from the first voltage to the second voltage.

17. The system of claim 16, wherein controlling the extract voltage applied to the cathode such that the current of the x-ray source peaks above the target current comprises increasing the extract voltage from a first extract voltage to a second extract voltage at a predetermined time after the voltage of the x-ray source begins transitioning from the first voltage to the second voltage.

18. The system of claim 16, wherein controlling the extract voltage applied to the cathode such that the current of the x-ray source peaks above the target current comprises gradually increasing the extract voltage from a first extract voltage to a second extract voltage at a predetermined rate while the voltage of the x-ray source is between the first voltage and the second voltage.

19. The system of claim 15, wherein the computing device is further configured with executable instructions in non-transitory memory that when executed cause the computing device to control the current to zero current when the voltage is transitioning from the second voltage to the first voltage.

20. The system of claim 15, wherein the computing device is further configured with executable instructions in non-transitory memory that when executed cause the computing device to receive, via the DAS, projection data for both the first beam of x-rays and the second beam of x-rays, and reconstruct an image from the projection data.

* * * * *